United States Patent [19]

Salmon

[11] Patent Number: 5,451,598
[45] Date of Patent: Sep. 19, 1995

[54] HETEROCYCLIC COMPOUNDS AND INSECTICIDAL USE

[75] Inventor: Roger Salmon, Bracknell, United Kingdom, RG12 4YU

[73] Assignee: Zeneca Limited, Millbank, United Kingdom

[21] Appl. No.: 211,232

[22] PCT Filed: Sep. 8, 1992

[86] PCT No.: PCT/GB92/01636
§ 371 Date: Aug. 1, 1994
§ 102(e) Date: Aug. 1, 1994

[87] PCT Pub. No.: WO93/06089
PCT Pub. Date: Apr. 1, 1993

[30] Foreign Application Priority Data
Sep. 27, 1991 [GB] United Kingdom ............ 9120641

[51] Int. Cl.⁶ ................. A01N 43/56; C07D 231/18
[52] U.S. Cl. ............................ 314/404; 314/407; 548/367.4; 548/369.4; 548/370.1
[58] Field of Search ............ 548/369.4, 370.1, 367.4; 514/404, 407

[56] References Cited
FOREIGN PATENT DOCUMENTS
234119 9/1987 European Pat. Off. .

OTHER PUBLICATIONS
Sheppard, J. A. C. S. 84, 3604–3075 (1962).
Jesith et al., Journal of Fluorine Chemistry 54, 111 (1991 (Abstract).

*Primary Examiner*—Robert W. Ramsuer
*Attorney, Agent, or Firm*—Joel G. Ackerman

[57] ABSTRACT

Compounds with insecticidal activity have the formula (I):

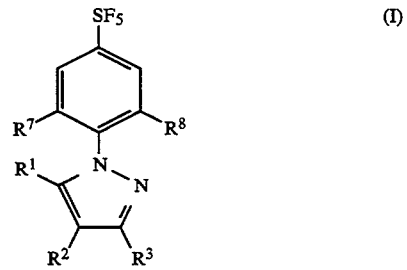

wherein $R^1$ is hydrogen, halogen, or a group $NR^4R^5$ wherein $R^4$ and $R^5$ are independently selected from hydrogen or alkyl; $R^2$ is a group $-S(O)_nR^6$ wherein n is 0, 1 or 2 and $R^6$ is a haloalkyl group; $R^3$ is $-CN$ or is a group $CX-NY^1Y^2$ for example $-CS-NH_2$; and $R^7$ and $R^8$, which may be the same or different, are halogen.

8 Claims, No Drawings

HETEROCYCLIC COMPOUNDS AND INSECTICIDAL USE

This application is a 371 of PCT/GB92/01636 Sep. 8, 1992.

This invention relates to heterocyclic compounds and in particular to pyrazole compounds to processes for their preparation and to their use as insecticides.

European Patent Application 0 295 117 discloses N-phenylpyazole derivatives having anthropodicidal, plant nematocidal, anthelmintic and anti-protozoal properties of general formula (i) wherein $R^1$ represents cyano, nitro, halogen, acetyl or formyl; $R^2$ represents $R^5SO_2$, $R^5SO$ or $R^5S$ in which $R^5$ is optionally halogen substituted alkyl, alkenyl or alkynyl; $R^3$ represents a hydrogen atom or a group $NR^6R^7$ wherein $R^6$ and $R^7$ each represent hydrogen, alkyl, alkenylalkyl, alkynylalkyl, formyl, optionally halogen substituted alkoxycarbonyl or alkoxymethyleneamino, halogen or $R^6$ and $R^7$ together form a cyclic imide and $R^4$ represents a substituted phenyl group.

European Patent Application 0 418 016 discloses similar N-phenylpyrazole derivatives of general formula (ii), wherein A represents an halogen atom chosen among iodine, bromine, the hydrogen atom or an amino group and m is the integer 1 or 2 with the exclusion of the compounds wherein A represents an amino group and n is zero.

The efficacy of certain insecticides against the target species, for example public health pests such as flies and cockroaches, may be reduced dramatically over a period of years as the target species develop resistance to the insecticide. Thus the presence of resistant strains of housefly and other public health pests in many parts of the world can be a serious problem and limits the use of insecticides such as lindane/dieldrin and more generally the general class of insecticides known as cyclodienes. Resistance can persist many years after an insecticide has ceased to be in widespread use and what is more, resistant strains of the target species may also prove to be resistant to novel insecticides. Such "cross-resistance" may mean that even a novel insecticide is effective only against susceptible strains of the target species and has relatively little effect on resistant strains. This can prove a serious limitation.

The present invention provides a class of novel insecticides which maintain a significant activity against lindane/dieldrin-resistant strains of public health pests.

According to the present invention there is provided a compound of formula (I) wherein $R^1$ is hydrogen, halogen, or a group $NR^4R^5$ wherein $R^4$ and $R^5$ are independently selected from hydrogen or alkyl; $R^2$ is a group $—S(O)_nR^6$ wherein n is 0, 1 or 2 and $R^6$ is a haloalkyl group; $R^3$ is $—CN$ or is a group $CX—NY^1Y^2$ wherein X is O or S or S=O; and $Y^1$ and $Y^2$ are independently selected from hydrogen, nitro, amino or alkyl optionally substituted by halogen, by cycloalkyl, by formyl, by $C_{2-7}$ alkanoyl, by $C_{4-7}$ cycloalkylcarbonyl, by $C_{2-7}$ alkoxycarbonyl, by $C_{2-7}$ haloalkoxycarbonyl, by an aryl group or by an aromatic heterocyclic group or $Y^1$ and $Y^2$ together with the nitrogen to which they are attached form an aliphatic heterocyclic group containing from 4 to 8 atoms in the ring and optionally substituted by halogen or alkyl or $Y^1$ and $Y^2$ together form the group $=CHY^3$ wherein $Y^3$ is alkyl, $C^{2-6}$ alkenyl, aryl, an aromatic heterocycle, or amino optionally substituted by alkyl or $Y^1$ is hydrogen and $Y^2$ is alkoxycarbonyl, alkylcarbonyl, optionally substituted aralkyl or a group $—S(O)_nR^6$ where $R^6$ and n are as hereinbefore defined; and $R^7$ and $R^8$, which may be the same or different, are halogen.

The term "alkyl" is used herein includes straight or branched chain alkyl groups, preferably containing up to 6 carbon atoms, for example from 1 to carbon atoms. This applies also to alkyl moieties contained in other groups such as "haloalkyl" groups. The term "cycloalkyl" used herein refers to a carbocyclic ring suitably having from 3 to 10 and preferably from 3 to 7 carbon atoms in the ring. The cycloalkyl group is preferably cyclopropyl.

Preferably $R^1$ is $NH_2$, $N(CH_3)_2$, hydrogen or halogen, for example chloro or bromo.

Preferably $R^6$ is a $C_1$-$C_4$ haloalkyl group, for example a halomethyl or haloethyl group. It is especially preferred that $R^6$ is a $C_1$-$C_4$ fluoroalkyl, chlorofluoroalkyl or a bromofluoroalkyl group, for example trifluoromethyl, pentafluoroethyl, chlorodifluoromethyl, dichlorofluoromethyl, difluoromethyl, difluoroethyl, or bromodifluoromethyl.

Preferably $R^3$ is $—CN$ or a group $—CS—NH_2$.

$R^7$ and $R^8$ are preferably independently selected from chloro and bromo.

Examples of compounds of formula (I) are set out in Table I below.

TABLE I

| Compound | $R^1$ | $R^2$ | $R^3$ | $R^7$ | $R^8$ |
|---|---|---|---|---|---|
| 1 | $NH_2$ | $SCF_3$ | CN | Cl | Cl |
| 2 | $NH_2$ | $SOCF_3$ | CN | Cl | Cl |
| 3 | $NH_2$ | $SO_2CF_3$ | CN | Cl | Cl |
| 4 | $NH_2$ | $SCCl_2F$ | CN | Cl | Cl |
| 5 | $NH_2$ | $SOCCl_2F$ | CN | Cl | Cl |
| 6 | $NH_2$ | $SO_2CCl_2F$ | CN | Cl | Cl |
| 7 | $NH_2$ | $SCClF_2$ | CN | Cl | Cl |
| 8 | $NH_2$ | $SOCClF2$ | CN | Cl | Cl |
| 9 | $NH_2$ | $SO_2ClCF2$ | CN | Cl | Cl |
| 10 | $NH_2$ | $SCF_3$ | $—CS—NH_2$ | Cl | Cl |
| 11 | H | $SCF_3$ | CN | Cl | Cl |
| 12 | H | $SOCF_3$ | CN | Cl | Cl |
| 13 | H | $SO_2CF_3$ | CN | Cl | Cl |
| 14 | H | $SCCl_2F$ | CN | Cl | Cl |
| 15 | H | $SOCCl_2F$ | CN | Cl | Cl |
| 16 | H | $SO_2CCl_2F$ | CN | Cl | Cl |
| 17 | H | $SCClF_2$ | CN | Cl | Cl |
| 18 | H | $SOClF_2$ | CN | Cl | Cl |
| 19 | H | $SO_2ClCF_2$ | CN | Cl | Cl |
| 20 | I | $SCF_3$ | CN | Cl | Cl |
| 21 | I | $SOCF_3$ | CN | Cl | Cl |
| 22 | I | $SO_2CF_3$ | CN | Cl | Cl |
| 23 | I | $SCCl_2F$ | CN | Cl | Cl |
| 24 | I | $SOCCl_2F$ | CN | Cl | Cl |
| 25 | I | $SO_2CCl_2F$ | CN | Cl | Cl |
| 26 | I | $SCClF_2$ | CN | Cl | Cl |
| 27 | I | $SOClF_2$ | CN | Cl | Cl |
| 28 | I | $SO_2ClCF_2$ | CN | Cl | Cl |
| 29 | Br | $SCF_3$ | CN | Cl | Cl |
| 30 | Br | $SOCF_3$ | CN | Cl | Cl |
| 31 | Br | $SO_2CF_3$ | CN | Cl | Cl |
| 32 | Br | $SCCl_2F$ | CN | Cl | Cl |
| 33 | Br | $SOCCl_2F$ | CN | Cl | Cl |
| 34 | Br | $SO_2CCl_2F$ | CN | Cl | Cl |
| 35 | Br | $SCClF_2$ | CN | Cl | Cl |
| 36 | Br | $SOClF_2$ | CN | Cl | Cl |
| 37 | Br | $SO_2ClCF_2$ | CN | Cl | Cl |
| 38 | $N(CH_3)_2$ | $SCF_3$ | CN | Cl | Cl |
| 39 | $NH_2$ | $SCF_3$ | CN | Br | Br |
| 40 | $NH_2$ | $SOCF_3$ | CN | Br | Br |
| 41 | $NH_2$ | $SO_2CF_3$ | CN | Br | Br |
| 42 | $NH_2$ | $SCF_3$ | $CS—NH_2$ | Br | Br |
| 43 | H | $SCF_3$ | CN | Br | Br |
| 44 | Cl | $SCF_3$ | CN | Br | Br |
| 45 | $NH_2$ | $SCF_2H$ | CN | Cl | Cl |
| 46 | $NH_2$ | $SCF_2H$ | CN | Br | Br |
| 47 | $NH_2$ | $SCF_2CH_3$ | CN | Cl | Cl |

TABLE I-continued

| Compound | $R^1$ | $R^2$ | $R^3$ | $R^7$ | $R^8$ |
| --- | --- | --- | --- | --- | --- |
| 48 | $NH_2$ | $SCF_2CH_3$ | CN | Br | Br |
| 49 | $NH_2$ | $SCF_2Br$ | CN | Cl | Cl |
| 50 | $NH_2$ | $SCF_2Br$ | CN | Br | Br |

Also to be considered as specifically disclosed are compounds corresponding to Nos 1 to 9, 11 to 41 and 43 to 44 above in which $R^3$ is the group —CS—$NH_2$ in place of —CN. Also to be considered as specifically disclosed are compounds corresponding to Nos 1 to 38 in which $R^7$ and $R^8$ are Br in place of Cl.

Compounds of formula (I) may be prepared by (A) reacting a compound of formula (II) with a compound of formula (III) to form a compound of formula (IV) which then undergoes a cyclisation reaction (B), for example in the presence of ammonia to yield a compound of formula (V). Treatment of (V) with a thioalkylating agent or thiohaloalkylating agent such as the compound $R^6SCl$ where $R^6$ is as previously defined gives a compound of formula (I) wherein $R^1$ is $NH_2$, $R^2$ is $R^6(O)nS$ wherein 0, and $R^3$ is CN; i.e. a compound of formula (VI) wherein n is 0.

Compounds wherein $R^1$ is halogen may be prepared by diazotising the group —$NH_2$ in a compound of formula (I) wherein $R^1$ is $NH_2$ followed by reaction with a halogenating agent such as a halogen halide. A suitable diazotising agent is tert-butyl nitrite in a solvent such as acetonitrile and the reaction suitably takes place under an inert atmosphere. The halogenating agent, for example copper II halide, may be present during the course of the reaction. Alternatively compounds wherein $R^1$ is halogen may be prepared by halogen exchange, for example by the reaction of a compound wherein $R^1$ is Bromo with a fluoride salt such as potassium or cesium fluoride.

Compounds wherein $R^1$ is hydrogen may be prepared by reducing the group —$NH_2$ in a compound of formula (I) wherein $R^1$ is —$NH_2$, for example using tert. butyl nitrite in a solvent such as tetrahydrofuran. Reduction of the group —$NH_2$ may take place during the diazotisation reaction mentioned above, and a compound wherein $R^1$ is hydrogen may be a co-product of the halogenation reaction.

Compounds wherein $R^2$ is the group $R^6(O)_nS$ and n is 1 and 2 may be prepared by oxidising the group $R^6(O)nS$ in a compound of formula (I) wherein $R^2$ is the group $R^6(O)_nS$ and n is 0. Numerous suitable oxidising agents will occur to those skilled in the art. Examples include peracetic acid, pertrifluoroacetic acid, hydrogen peroxide and meta chloroperbenzoic acid. The product of the oxidation may be the S-oxide or S-dioxide or a mixture thereof, according to the conditions employed.

Compounds wherein $R^3$ is a group —CS—$NH_2$ may be prepared by treating the group —CN in a compound of formula (I) wherein $R^3$ is —CN with a thioamidating agent. A suitable thioamidating agent is hydrogen sulphide in the presence of a base, for example an amine such as pyridine or triethylamine. Altenatively, a compound of formula (I) wherein $R^3$ is —CN may be reacted with a compound or formula alkyl—CS—$NH_2$, for example thioacetamide, in the presence of dry gaseous hydrogen chloride. A suitable solvent for the reaction is dimethylformamide.

Compounds wherein $R^1$ is a group —$N(R^4R^5)$ when $R^1$ is a group —$N(R^4R5)$ wherein at least one of $R^4$ and $R^5$ is alkyl may be prepared by treating the group —$NH_2$ in a compound of formula (I) wherein $R^1$ is $NH_2$ with an alkylating agent such as dimethyl sulphate, optionally in the presence of a phase transfer catalyst such as benzyltributylammonium chloride.

Compound (II) may be prepared by halogenation of 4-aminophenylsulphurpentafluoride, the preparation of which is reported in the Journal of the American Chemical Society 84 3064 (1962)).

According to a further aspect of the present invention there is provided a compound of formula (V).

According to a further aspect of the present invention there is provided a compound of formula (IV).

According to a further aspect of the present invention there is provided a compound of formula (II)

The compounds of formula (I) may be used to combat and control infestations of insect pests and also other invertebrate pests, for example, acarine pests. The insect and acarine pests which may be combated and controlled by the use of the invention compounds include those pests associated with agriculture (which term includes the growing of crops for food and fibre products), horticulture and animal husbandry, forestry, the storage of products of vegetable origin, such as fruit, grain and timber, and also those pests associated with the transmission of diseases of man and animals.

In order to apply the compounds to the locus of the pests they are usually formulated into compositions which include in addition to the insecticidally active ingredient or ingredients of formula I suitable inert diluent or carrier materials, and/or surface active agents. The compositions may also comprise another pesticidal material, for example another insecticide or acaricide, or a fungicide, or may also comprise an insecticide synergist, such as for example dodecyl imidazole, safroxan, or piperonyl butoxide.

The compositions may be in the form of dusting powders wherein the active ingredient is mixed with a solid diluent or carrier, for example kaolin, bentonite, kieselguhr, or talc, or they may be in the form of granules, wherein the active ingredient is absorbed in a porous granular material for example pumice.

Alternatively the compositions may be in the form of baits wherein the active ingredient is mixed with a nutrient carrier for example sucrose, yeast, malt extract, cereal or cereal products and optionally an attractant such as a pheromone or pheromone analogue.

Alternatively the compositions may be in the form of liquid preparations to be used as dips or sprays, which are generally aqueous dispersions or emulsions of the active ingredient in the presence of one or more known wetting agents, dispersing agents or emulsifying agents (surface active agents).

Wetting agents, dispersing agents and emulsifying agents may be of the cationic, anionic or non-ionic type. Suitable agents of the cationic type include, for example, quaternary ammonium compounds, for example cetyltrimethyl ammonium bromide. Suitable agents of the anionic type include, for example, soaps, salts of aliphatic monoesters of sulphuric acid, for example sodium lauryl sulphate, salts of sulphonated aromatic compounds, for example sodium dodecylbenzenesulphonate, sodium, calcium or ammonium lignosulphonate, or butylnaphthalene sulphonate, and a mixture of the sodium salts of diisopropyl- and triisopropylnaphthalene sulphonates. Suitable agents of the non-ionic type include, for example, the condensation products of ethylene oxide with fatty alcohols such as oleyl alcohol or cetyl alcohol, or with alkyl phenols such as octyl phenol, nonyl phenol and octyl cresol. Other non-ionic agents are the partial esters derived from long chain fatty acids and hexitol anhydrides, the condensation products of the said partial esters with ethylene oxide, and the lecithins.

The compositions may be prepared by dissolving the active ingredient in a suitable solvent, for example, a ketonic solvent such as diacetone alcohol, or an aromatic solvent such as trimethylbenzene and adding the mixture so obtained to water which may contain one or more known wetting, dispersing or emulsifying agents.

Other suitable organic solvents are dimethyl formamide, ethylene dichloride, isopropyl alcohol, propylene glycol and other glycols, diacetone alcohol, toluene, kerosene, white oil, methylnaphthalene, xylenes and trichloroethylene, N-methyl-2-pyrrolidone and tetrahydrofurfuryl alcohol (THFA).

The compositions which are to be used in the form of aqueous dispersions or emulsions are generally supplied in the form of a concentrate containing a high proportion of the active ingredient or ingredients, the said concentrate to be diluted with water before use. These concentrates are often required to withstand storage for prolonged periods and after such storage, to be capable of dilution with water to form aqueous preparations which remain homogeneous for a sufficient time to enable them to be applied by conventional spray equipment. The concentrates may contain 10–85% by weight of the active ingredient or ingredients. When diluted to form aqueous preparations such preparations may contain varying amounts of the active ingredient depending upon the purpose for which they are to be used. For agricultural or horticultural purposes, an aqueous preparation containing between 0.0001% and 0.1% by weight of the active ingredient (approximately equivalent to from 5–2000 g/ha) is particularly useful.

In use the compositions are applied to the pests, to the locus of the pests, to the habitat of the pests, or to growing plants liable to infestation by the pests, by any of the known means of applying pesticidal compositions, for example, by dusting or spraying.

The compounds of the invention may be the sole active ingredient of the composition or they may be admixed with one or more additional active ingredients such as insecticides, insecticide synergists, herbicides, fungicides or plant growth regulators where appropriate. Suitable additional active ingredients for inclusion in admixture with the compounds of the invention may be compounds which will broaden the spectrum of activity of the compounds of the invention or increase their persistence in the location of the pest. They may synergise the activity of the compound of the invention or complement the activity for example by increasing the speed of effect, improving knockdown or overcoming repellency. Additionally multi-component mixtures of this type may help to overcome or prevent the development of resistance to individual components.

The particular insecticide, herbicide or fungicide included in the mixture will depend upon its intended utility and the type of complementary action required. Examples of suitable insecticides include the following:

a) Pyrethroids such as permethrin, esfenvalerate, deltamethrin, cyhalothrin in particular lambda-cyhalothrin, cypermethrin, alpha cypermethrin, biphenthrin, fenpropathrin, cyfluthrin, tefluthrin, fish safe pyrethroids for example ethofenprox, natural pyrethrin, tetramethrin, s-bioallethrin, fenfluthrin, prallethrin, and 5-benzyl-3-furylmethyl-(E)-(1R,3S)-2,2-dimethyl-3-(2-oxothiolan-3-ylidenemethyl) cyclopropane carboxylate;

b) Organophosphates such as profenofos, sulprofos, methyl parathion, azinphos-methyl, demeton-s-methyl, heptenophos, thiometon, fenamiphos, monocrotophos, profenophos, triazophos, methamidophos, dimethoate, phosphamidon, malathion, chloropyrifos, phosalone, fensulfothion, fonofos, phorate, phoxim, pyrimiphos-methyl, fenitrothion or diazionon;

c) Carbamates (including aryl carbamates) such as pirimicarb, cloethocarb, carbofuran, ethiofencarb, aldicarb, thiofurox, carbosulfan, bendiocarb, fenobucarb, propoxur or oxamyl;

d) Benzoyl ureas such as triflumeron, or chlorofluazuron;

e) Organic tin compounds such as cyhexatin, fenbutatin oxide, azocyclotin;

f) Macrolides such as avermectins or milbemycins, for example such as avamectin, avermectin, and milbemycin;

g) Hormones such as pheromones;

h) Organochlorine compounds such as benzene hexachloride, DDT, chlordane or dieldrin.

i) Amidines, such as chlordimeform or amitraz.

In addition to the major chemical classes of insecticide listed above, other insecticides having particular targets may be employed in the mixture if appropriate for the intended utility of the mixture. For instance selective insecticides for particular crops, for example stemborer specific insecticides for use in rice such as cartap or buprofezin can be employed. Alternatively insecticides specific for particular insect species/stages for example ovo-larvicides such as chofentezine, flubenzimine, hexythiazox and tetradifon, moltilicides such as dicofol or propargite, acaricides such as bromopropylate, chlorobenzilate, or growth regulators such as hydramethylon, cyromazin, methoprene, chlorofluazuron, hydroprene and diflubenzuron may also be included in the compositions.

Examples of suitable insecticide synergists for use in the compositions include piperonyl butoxide, sesamex, and dodecyl imidazole.

Suitable herbicides, fungicides and plant-growth regulators for inclusion in the compositions will depend upon the intended target and the effect required. An example of a rice selective herbicide which can be included is propanil, an example of a plant growth regulator for use in cotton is "Pix", and examples of fungicides for use in rice include blasticides such as blasticidin-S.

The ratio of the compound of the invention to the other active ingredient in the composition will depend upon a number of factors including type of target, effect required from the mixture etc.

However in general, the additional active ingredient of the composition will be applied at about the rate as it is usually employed, or at a slightly lower rate if synergism occurs.

The compounds of formula I and compositions comprising them have shown themselves active against a variety of insect and other invertebrate pests. They are particularly useful in controlling public health pests such as flies and cockroaches. Compounds of the present invention are also generally characterised by a relatively broad spectrum of activity which may include Lepidoptera and Coleoptera in addition to public health pests.

They may also be active against organophosphate, pyrethroid, cyclodiene (for example lindane or dieldrin) resistant strains of public and animal health pests. They may be effective in combating both susceptible and resistant strains of the pests in their adult and immature stages of growth, and may be applied to the infested host animal by topical, oral or parenteral administration.

The following Examples illustrate various aspects of this invention. In the Preparations and Examples the products were usually identified and characterised by means of nuclear magnetic resonance spectroscopy. In each case where a product is specifically named its spectral characteristics are consistent with the assigned structure.

EXAMPLE 1

This Example illustrates the preparation of 5-amino-3-cyano-4-trifluoromethylthio-1-(2,6-dichloro-4-sulphurpentafluorophenyl)pyrazole (Compound No 1 of Table 1).

Stage 1

4-Nitrophenylsulphurpentafluoride was prepared using the method of Sheppard (*JACS* 84 3064 (1962)) and the crude product was purified by eluting through a short column of silica gel with hexane/ethyl acetate (100:2 by volume).

The purified product (2.30 g) in ethanol (28 ml) and ethanolic hydrogen chloride solution (1.75 cm$^3$; 5.5 M) was treated with platinum oxide (catalyst; 0.084 g) and hydrogen at 3 atmospheres of pressure with stirring.

After 5 hours the catalyst was filtered from solution, washed with ethanol and the filtrate evaporated under reduced pressure to give 4-aminophenylsulphurpentafluoride hydrochloride as an off-white solid.

Stage 2

The product of stage 1 (2.0 g) was suspended in concentrated hydrochloric acid (15 cm$^3$) with ice bath cooling, and hydrogen peroxide (2.2 cm$^3$; 30% by weight in water) was added dropwise to the stirred mixture. On complete addition the reaction was allowed to slowly warm to ambient temperature and stirred for a further 2 hours. The mixture was treated with sodium hydroxide solution (2M) until basic, extracted with ethyl acetate (three times), dried over anhydrous magnesium sulphate and evaporated under reduced pressure to give 4-amino-3,5-dichlorophenylsulphurpentafluoride (2.05 g) as a brown liquid. Molecular ion 287. NMR (CDCl$_3$): $\delta$7.60 (s,2H); 4.80 (broad s,2H).

Stage 3

The product of Stage 2 (1.00 g) in acetic acid (2.5 cm$^3$) was added at 25°-30° C. over 30 minutes to a previously prepared solution of sodium nitrite (0.265 g) in concentrated sulphuric acid (1.4 cm$^3$) and glacial acetic acid (1.25 cm$^3$), held at 35°-40° C. and then cooled to ambient temperature.

On complete addition the stirred mixture was heated to 55° C. for 30 minutes, cooled to ambient temperature, and added to a mixture of ethyl 1,2-dicyano propionate (0.64 g), acetic acid (3 cm$^3$) and water (6.25 cm$^3$) at 10°-20° C. The reaction mixture was stirred at ambient temperature for 20 minutes, poured into water (15 cm$^3$) and extracted with dichloromethane (3×7 cm$^3$). The combined extracts were washed with aqueous (0.88) ammonia (1.5 cm$^3$) and the organic phase treated with further ammonia solution (1 cm$^3$) and stirred for 18 hours at ambient temperature. The organic phase was separated, washed with water (twice), dried over anhydrous magnesium sulphate and evaporated under reduced pressure to give a brown gum. The gum was fractionated by eluting through a short column of silica gel with dichloromethane/hexane (3:1 by volume) to give 5-amino-3-cyano-1(2,6-dichloro-4-sulphurpentafluorophenyl)-pyrazole as a pale yellow solid. NMR (CDCl$_3$): $\delta$7.93(s,2H), 6.05(s,1H), 3.7–3.8(broad singlet,NH$_2$). Molecular ion 378.

Stage 4

The product of stage 3 (0.29 g) in dry dichloromethane (8 cm$^3$) was stirred and cooled to −14° C. Trifluoromethylsulphenyl chloride was slowly bubbled into the solution and retained at reflux using a carbon dioxide/acetone cold trap. The solution was allowed to reach ambient temperature and was stirred for 1½ hours, poured into water (50 cm$^3$) and treated with aqueous sodium hydrogen carbonate. The mixture was extracted with diethyl ether (three times) and the combined extracts washed with water, dried over anhydrous magnesium sulphate and evaporated under reduced pressure to give a pale yellow solid. The solid was fractionated by eluting through a short column of silica gel with dichloromethane/hexane (1:1 by volume) to give the desired product as a colourless solid. Melting point 184.9°-186.8°: NMR CDCl$_3$ $\delta$7.95(2H,s); 4.35–4.50(broad singlet,2H). Molecular ion 478.

EXAMPLE 2

This Example illustrates the preparation of 5-amino-3-cyano-1-(2,6-dichloro-4-sulphurpentafluorophenyl)-pyrazol-4-yl-(trifluoromethyl-S-dioxide) (Compound No 2 of Table 1) and 5-amino-3-cyano-1-(2,6-dichloro-4-sulphurpentafluorophenyl)-pyrazol-4-yl-(trifluoromethyl-S-dioxide) (Compound No 3 of Table 1).

5-Amino-3-cyano-1(2,6-dichloro-4-sulphurpentafluorophenyl)-4-trifluoro methylthiopyrazole (Example 1—0.15 g) in dichloromethane (6 cm$^3$) was stirred at ambient temperature and treated with meta chloroperbenzoic acid (0.108g, 50–60%; solution in dichloromethane). After 16 hours further meta chloroperbenzoic acid (0.054 g) was added and the reaction kept for a total of 30 hours at ambient temperature. The reaction mixture was washed with aqueous sodium hydrogen carbonate solution, dried over anhydrous magnesium sulphate and evaporated under reduced pressure to give a pale yellow solid. The solid was fractionated by eluting through a short column of silica gel using hexane/dichloromethane (3:7 by volume) to give 5-amino-3-cyano-1(2,6-dichloro-4-sulphurpentafluorophenyl)-pyrazol-4-yl-trifluoromethyl-S-oxide. Melting point 220.5°-221.6° C.; $^1$H NMR $\delta$(DMSO) 7.50–7.55 (broad signal, 2H); 8.50 (s, 2H) and 5-amino-3-cyano-1-(2,6-dichloro-4-sulphurpentafluorophenyl)-pyrazol-4-yl-trifluoromethyl-S-dioxide; Melting point 242.5°-245.8° C.; $^1$H NMR $\delta$(DMSO) 8.0 (broad signal, 2H); 8.50 (s, 2H).

EXAMPLE 3

This Example illustrates the preparation of 5-amino-3thiocarboxamido-4-trifluoromethylthio-1-(2,6-dichloro-4-sulphurpentafluorophenyl)pyrazole (Compound No 10 of Table 1).

Triethylamine (0.032 g) was added to a solution of 5-amino-3-cyano-1-(2,6-dichloro-4-sulphurpentafluorophenyl)pyrazole (prepared as in Example 1; 0.150 g) in dry toluene (10 cm$^3$) the mixture was stirred with excess hydrogen sulphide gas bubbled through for 30 minutes. The reaction flask was sealed, stirred for 2 hours at ambient temperature and then stored for 16 hours.

The solvent was evaporated under reduced pressure to give a yellow solid. This solid was fractionated by column chromatography (silica; eluted with dichloromethane) to give the desired product as a pale yellow solid; Melting point 117.2°–117.9° C. $^1$HNMR (CDCl$_3$) 7.9 and 7.3 [overlapping signals; 3H] 4.3 [broad signal; 2H]. Molecular ion 513.

EXAMPLE 4

This Example illustrates the preparation of 5-bromo-3-cyano-4-trifluoromethylthio-1-(2,6-dichloro-4-sulphurpentafluorophenyl) pyrazole (Compound No 29 of Table 1) and 3-cyano-4-trifluoromethylthio-1-(2,6-dichloro-4-sulphurpentafluorophenyl)pyrazole (Compound No 11 of Table 1).

A solution of tert-butylnitrite (0.259 g) in dry acetonitrile (2 cm$^3$) was added slowly dropwise to a cooled solution of copper II bromide (0.330 g) in dry acetonitrile (4 cm$^3$) under an inert atmosphere of nitrogen.

5-Amino-3-cyano-1-(2,6-dichloro-4-sulphurpentafluorophenyl)-4-trifluoromethylthiopyrazole (Example 1; 0.300 g) in dry acetonitrile (5 cm$^3$) was added, the mixture stirred for 2 hours, allowed to reach ambient temperature and stirred for an additional 18 hours.

The reaction mixture was poured into water, treated with 2M hydrochloric acid (4 drops) and extracted with ethyl acetate (3 times). The organic extracts were combined, washed with water (2 times), dried over anhydrous magnesium sulphate and evaporated under reduced pressure to give a yellow solid. This solid was fractionated by column chromatography (silica eluted with hexane/ethyl acetate; 97:3 by volume) to give 5-bromo-3-cyano-4-trifluoromethylthio-1-(2,6-dichloro-4-sulphurpentafluorophenyl)pyrazole as a colourless solid. Melting point 142.6°–143.8° C.; $^1$HNMR δ(CDCl$_3$) 7.98(s); Molecular ion 541

Elution with hexane/ethyl acetate (9:1 by volume) gave 3-cyano-4-trifluoromethylthio-1-(2,6-dichloro-4-sulphurpentafluorophenyl)pyrazole as a pale yellow solid. Melting point 112.9°–113.7° C.; $^1$HNMR δ(CDCl$_3$) 7.93(s,2H), 7.95(s,1H); molecular ion 463.

EXAMPLE 5

This Example illustrates the preparation of 3-cyano-5-N',N'dimethylamino-4-trifluoromethylthio-1-(2,6-dichloro-4-sulphurpentafluorophenyl)-pyrazole (Compound No 38 in Table 1).

Aqueous (40%) sodium hydroxide solution (6.5 cm$^3$) was added to a solution of 5-amino-3-cyano-4-trifluoromethylthio-1-(2,6-dichloro-4-sulphurpentafluorophenyl)pyrazole (Example 1; 0.150 g) in dry dichloromethane (15 cm$^3$). Benzyltributylammonium chloride (3 mg) was added, followed by dimethylsulphate (0.065 cm3). The reaction mixture was stirred at ambient temperature for 24 hours and another portion of dimethylsulphate (0.01 cm$^3$) added. The reaction mixture was stirred for a further 16 hours. Dichloromethane (10cm$^3$) was added, and the organic phase was separated and evaporated under reduced pressure to give a yellow solid. This solid was dissolved in ethanol (1 cm$^3$) and treated with aqueous (0.88) ammonia (0.1 cm$^3$) and the mixture was stirred at ambient temperature for 5 hours.

Dichloromethane (30cm3) was added and the organic phase was washed with saturated aqueous sodium chloride. The organic phase was dried over anhydrous magnesium sulphate and evaporated under reduced pressure to give a yellow solid.

This solid was fractionated by eluting through a short column of silica gel using hexane/dichloromethane (95:5 by volume) to give 3-cyano-5-N', N'-dimethylamino-4-trifluoromethylthio-1-(2,6-dichloro-4-sulphurpentafluorophenyl) pyrazole as a colourless solid. Melting point 109.1°–111.4° C.; $^1$HNMR δ(CDCl$_3$) 7.90(s,2H), 2.85(s,6H); Molecular ion 506.

EXAMPLE 6

This Example illustrates the preparation of 5-amino-4-chlorodifluoromethylthio-3-cyano-1-3-cyano1-(2,6-dichloro-4-sulphurpentafluorophenyl)pyrazole (Compound No 7 of Table 1) Stage 1

Difluorochlorosulphenylchloride was prepared using the method described by N. N. Yorovenko et al *J.Gen.-Chem* (USSR) (1959), 29, 2129–2130. The crude reaction product was dissolved in dry dichloromethane and used directly for stage 2.
Stage 2

The product from stage 1 was added to a solution of 5-amino-3-cyano-1-(2,6-dichloro-4-sulphurpentafluorophenyl)pyrazole (Example 1, Stage 3; 0.275 g) in dry dichloromethane (3 cm$^3$). The reaction mixture was stirred at ambient temperature for 88 hours. Saturated aqueous sodium bicarbonate (4 cm$^3$) was added and mixture stirred for 25 minutes. The layers were separated, and the aqueous layer was extracted with dichloromethane (2 times). The organic phases were combined, dried over anhydrous magnesium sulphate and evaporated under reduced pressure to give a yellow gum. The gum was fractionated by high performance liquid chromatography using hexane/dichloromethane (1:1 by volume) to give 5-amino-4-chlorodifluoromethylthio-3-cyano-1-(2,6-dichloro-4-sulphurpentafluorophenyl)pyrazole as a colourless solid. Melting point 175.9°–177.1° C. Molecular ion 494.

EXAMPLE 7

This Example illustrate the preparation of 5-amino-3-cyanol-(2,6-dichloro-4-sulphurpentafluorophenyl)-pyrazol-4-yl(chlorodifluoromethyl-S-oxide) Compound No 8 of Table 1).

5-Amino-4-chlorodifluoromethylthio-3-cyano-1-(2,6-dichloro-4-sulphurpentafluorophenyl)pyrazole (Example 6) was treated with 1 equivalent of Meta chloroperbenzoic acid using the general procedure of Example 2 to give the desired product. Melting point 225.5°–226.6° C.; $^1$HNMR δ(CDCl$_3$) 7.95(s,2H), 5.15–5.25(broad s, 2H); Molecular ion MH+511.

EXAMPLE 8

This Example illustrates the preparation of 5-amino-3-cyano-4-trifluoromethylthio-1-(2,6-dibromo-4-sulphurpentafluorophenyl)pyrazole (compound No. 39 of Table 1).
Stage 1

4-Aminophenylsulphurpentafluoride hydrochloride (prepared as is in Example 1, stage 1) was basified with a minimum of saturated aqueous sodium hydrogen carbonate. The mixture was extracted with diethyl ether, the extract dried over magnesium sulphate, and evaporated under reduced pressure to give 4-aminophenylsulphurpentafluoride as brown oil. Molecular ion 219; $^1$HNMR (CDCl$_3$): δ7.53(d,2H), 6.22(d,2H), 4.0(broad signal, 2H).
Stage 2

The product of stage 1 (0.96 g) was dissolved in a solution of sodium acetate trihydrate (3 g) in glacial acetic acid (15 cm$^3$). A solution of bromine (1.8 g) in glacial acetic acid (5 cm³) was added dropwise during 15 minutes, with rapid stirring, at 26°–32° C. Stirring was continued for 2 hours at ambient temperature. Saturated aqueous sodium hydrogen sulphate (2 cm³) was added and the mixture was concentrated under reduced pressure, basified with a minimum of dilute aqueous sodium hydroxide and extracted with diethyl ether (4×30cm³). The combined ether extracts were dried over magnesium sulphate and evaporated under reduced pressure to give 4-amino-3,5-dibromophenylsulphurpentafluoride (1.16 g) as a dark oil. Molecular ion 375.

Stage 3

The product of stage 2 was treated using the general procedure of Example 1 stage 3 to give 5-amino-3-cyano-1-(2,6-dibromo-4-sulphurpentafluorophenyl)-pyrazole as a colourless solid. Melting point 206°–207° C.; $^1$HNMR (D$_6$-DMSO): $\delta$8.47(2H,s), 6.06(2H,broad singlet), 5.88(1H,s); Molecular ion 466.

Stage 4

The product stage 3 was treated using the general procedure of Example 1, stage 4 to give the desired product as a colourless solid, melting point 194°–195° C.; $^1$HNMR (D$_6$-DMSO): $\delta$8.50(2H,s), 7.15 (2H, broad singlet); Molecular ion 566.

EXAMPLE 9

5-Amino-3-cyano-4-trifluoromethylthio-1-(2,6-dibromo-4-sulphurpentafluorophenyl)pyrazole (Example 8) was oxidised using the general procedure of Example 2 to give (a) 5-amino-3-cyano-1-(2,6-dibromo-4-sulphurpentafluorophenyl-pyrazol-4-yl-(trifluoromethyl-S-oxide) (Compound No. 40 of Table) as a colourless solid, melting point 222°–223 C.; $^1$HNMR(CDCl$_3$): $\delta$8.15(s,2H), 5.15(broad signal,2H); mass spectrum: M—O 566, M—CF$_3$ 513, M—O—CF$^3$ 497 and (b) 5-amino-3-cyano-1-(2,6-dibromo-4-sulphurpentafluorophenyl)pyrazol-4-yl-(trifluoromethyl-S-dioxide) (Compound No 41 of Table 1) as a colourless solid, melting point 245°–247° C.; $^1$HNMR(CDCl$_3$/D$_4$-MeOH): $\delta$8.16(s). Molecular ion 598.

EXAMPLE 10

5-Amino-3-cyano-4-trifluoromethylthio-1-(2,6-dibromo-4-sulphurpentafluorophenyl)pyrazole (Example 8) was treated using the general procedure of Example 3 to give 5-amino-3-thiocarboxamido-4-trifluoromethylthio-1-(2,6dibromo-4-sulphurpentafluorophenyl)pyrazole (Compound No 42 of Table 1) as a yellow solid, melting point 182°–185° C.; $^1$HNMR (CDCl$_3$) $\delta$8.13(s,2H), 7.98(broad signal,1H), 7.43(broad signal,1H), 4.35(broad signal,2H); Molecular ion 600.

EXAMPLE 11

5-Amino-3-cyano-4-trifluoromethylthio-1-(2,6-dibromo-4-sulphurpentafluorophenyl)pyrazole (Example 8) was treated using the general procedure of Example 4 except that copper II chloride was used in place of copper II bromide to give (a) 5-chloro-3-cyano-4-trifluoromethylthio-1-(2,6-dibromo-4-sulphurpentafluorophenyl)pyrazole (compound No. 42 of Table 1) as a colourless solid, melting point 149°–150° C.; $^1$HNMR (CDCl$_3$): $\delta$8.14(s) and (b) 3-cyano-4-trifluoromethylthio-1-(2,6-dibromo-4-sulphurpentafluorophenyl)-pyrazole (Compound No. 44 of Table 1) as a yellow solid, melting point 98°–99° C.; $^1$HNMR (CDCl$_3$): $\delta$8.13(2H,5), 7.94(1H,s); Molecular ion 551.

EXAMPLE 12

The activity of the compounds of formula (I) was determined using a variety of pests. The pests were treated with a liquid composition containing 500 parts per million (ppm) by weight of the compound unless otherwise stated. The compositions were made by dissolving the compound in acetone and diluting the solutions with water containing 0.01% by weight of a wetting agent sold under the trade name "SYNPERONIC" NX until the liquid composition contained the required concentration of the compound. "SYNPERONIC"is a Registered Trade Mark.

The test procedure adopted with regard to each pest was basically the same and comprised supporting a number of the pests on a medium which was usually a host plant or a foodstuff on which the pests feed, and treating either or both the medium and the pests with the compositions. The mortality of the pests was then assessed at periods usually varying from one to three days after the treatment.

The results of the tests are presented in Table II for each of the compounds at the rate in parts per million given in the second column. The results indicate a grading of mortality designated as A, B or C wherein A indicates 80–100% mortality, B indicates 50–79% mortality and C indicates less than 50% mortality.

Information regarding the pest species, the support medium or food, and the type and duration of the test is given in Table II. The pest species is designated by a letter code.

In Table III the pest organism used is designated by a letter code and the pest species, the support medium or food, and the type and duration of test is given.

TABLE II

| COM-POUND | RATE OF APPLICATION ppm | SPECIES | | | | |
|---|---|---|---|---|---|---|
| | | MD | BG | MP | HV | DB |
| | | | | (See Table III) | | |
| 1 | 500 | A | A | A | A | A |
| 2 | 500 | A | A | C | A | A |
| 3 | 500 | A | A | C | A | B |
| 7 | 500 | A | — | A | A | A |
| 8 | 500 | A | — | A | A | A |
| 10 | 500 | A | — | A | A | A |
| 11 | 500 | A | — | A | A | A |
| 29 | 500 | A | — | A | A | A |
| 38 | 500 | A | — | A | A | A |
| 39 | 500 | A | — | A | A | A |
| 40 | 500 | A | — | A | A | A |
| 41 | 500 | A | — | A | A | A |
| 42 | 500 | A | — | A | A | A |
| 43 | 500 | A | — | A | A | B |
| 44 | 500 | A | — | C | B | A |

TABLE III

| CODE LETTERS | TEST SPECIES | SUPPORT MEDIUM/FOOD | TYPE OF TEST | DURATION (days) |
|---|---|---|---|---|
| MD | Musca domestica (houseflies - adults) | Cotton wool/ sugar | Contact | 2 |
| BG | Blattella germanica (cockroach nymphs) | Plastic pot/ calf weaner pellets | Contact | 3 |

TABLE III-continued

| CODE LETTERS | TEST SPECIES | SUPPORT MEDIUM/FOOD | TYPE OF TEST | DURATION (days) |
|---|---|---|---|---|
| MP | *Myzus persicae* (green peach aphid) | Chinese Cabbage leaf | Contact | 3 |
| HV | *Heliothis virescens* (Tobacco budworm) | Soya leaf | Residual | 5 |
| DB | *Diabrotica balteata* (cucumber beetle - larvae) | Filter paper/ maize seed | Residual | 2 |

EXAMPLE 13

This Example illustrates the activity of compounds of the present invention against both susceptible and cyclodiene-resistant strains of *Musca domestica* and compares the relative activity with that of a prior art compound and dieldrin. Cypermethrin was used as internal standard. The susceptible strain was *Musca domestica* WHO strain and the cyclodiene-resistant strain was *Musca domestica* Cooper Dield strain (Rothamstead Experimental Station).

Methodology

Twenty 3-day old female *Musca domestica* were placed in conex cups with a sugar cube: each cup was covered with a 1 mm mesh net.

The appropriate weight of the compound under test was dissolved in 2 cm³ of a 50:50 mixture of ethanol and acetone, then diluted to give the required range of concentrations with 0.1% Synperonic solution.

Two replicates at each concentration were sprayed using a Potter Tower (Burkhard Manufacturing Co. Ltd), 1 cm³ of solution being sprayed directly onto each cup. Replicate No. 1 at each concentration was sprayed first (ascending rates), followed by replicate No. 2.

The flies were assessed for knockdown after 15 minutes and then held at a constant 25° C. and 60% Relative Humidity and were provided with water ad libitum. The flies were then assessed for mortality after 48 hours.

Data were statistically analysed to generate LC50 values.

The results are presented in Table IV. Compound A of the prior art is 5-amino-3-cyano-4-trifluoromethylthio-1-(2,6-dichloro-4-trifluoromethylphenyl)-pyrazole (Compound No 1 of EP 0 295 117). Compound B of the prior art is 5-amino-3-cyano-1-(2,6-dichloro-4-trifluoromethylphenyl)-pyrazol-4-yl(trifluoromethyl-S-oxide) (Compound No 52 of EP 0 295 117).

The LC50 for the susceptible strain is indicated as "LC50, MD (sus)" and for the resistant strain as "LC50, MD (res)". All LC50 values are in parts per million. The "RESISTANCE RATIO" in Table IV is defined as the mean LC50 value for the resistant strain divided by the mean LC50 value for the susceptible strain. The "POTENCY" in Table IV is defined as the activity against the susceptible strain relative to the standard insecticide, cypermethrin (72% activive ingredient).

TABLE IV

| Compound Number | LC50 MD (SUS) | LC50 MD (RES) | RESISTANCE RATIO | POTENCY RELATIVE TO CYPERMETHRIN |
|---|---|---|---|---|
| 1 | 1.38* | 3.21* | 2.33 | 3.53* |
| A | 3.60* | 105.16* | 29.21 | 1.44* |
| 2 | 1.38 | — | — | 2.53 |
| B | 15.42* | 143.39* | 9.30 | 0.34* |
| Dieldrin | 10.18++ | 545.24++ | 53.56 | |

*indicates mean of three standard determinations
++indicates mean of two standard determinations

EXAMPLE 14

This Example illustrates the efficacy of compounds of the present invention against resistant strains of rice grain weevil (*Sitophilus oryzae*). The susceptible strain was a mixed laboratory culture (Reading University) and the resistant strain was Q5050 strain (Reading University).

The methodology was as follows:

Approximately 10 insects were placed on filter paper treated with the indicated rate of compound as a solution in acetone. The insects were maintained at 25° C. and 60% relative humidity and were assessed for mortality at 3 days after treatment. Three replicates were undertaken at each concentration. The results are presented in Table V.

TABLE V

| Compound Number | Rate of Application (ppm) | % Mortality |
|---|---|---|
| (i) SUSCEPTIBLE STRAIN | | |
| 1 | 10 | 100 |
|  | 2.5 | 85 |
| A | 10 | 100 |
|  | 2.5 | 100 |
| Dieldrin | 10 | 94 |
|  | 2.5 | 80 |
|  | 22 | |
| (ii) RESISTANT STRAIN | | |
| 1 | 500 | 100 |
|  | 125 | 100 |
| A | 500 | 100 |
|  | 125 | 36 |
| Dieldrin | 500 | 4 |
|  | 125 | 0 |

The mortality for the untreated control was 0% for both strains.

FORMULAE
(in description)

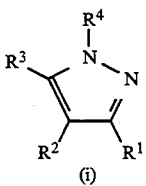

(i)

-continued
FORMULAE
(in description)

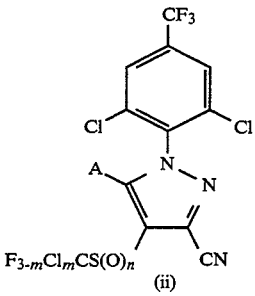
(ii)

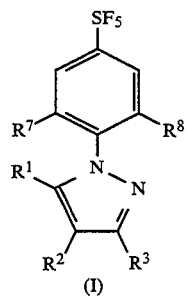
(I)

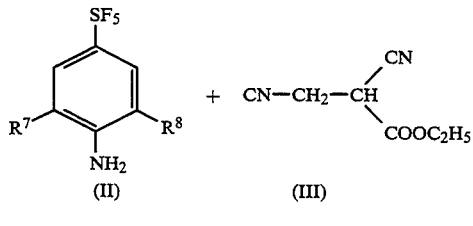
(A)

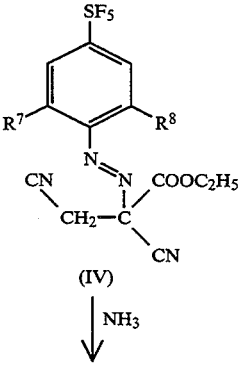
(B)

-continued
FORMULAE
(in description)

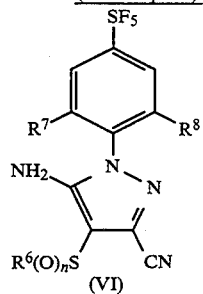
(VI)

I claim:
1. A compound of formula (I):

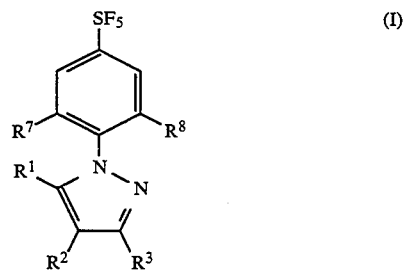

wherein $R^1$ is hydrogen, halogen, or a group $NR^4R^5$ wherein $R^4$ and $R^5$ are independently selected from hydrogen or alkyl; $R^2$ is a group $-S(O)_nR^6$ wherein n is 0, 1 or 2 and $R^6$ is a haloalkyl group; and $R^3$ is $-CN$ or is a group $CX-NY^1Y^2$ wherein X is O or S and $Y^1$ and $Y^2$ are independently selected from hydrogen, nitro, amino or alkyl optionally substituted by halogen, by cycloalkyl, by formyl, by $C_{2-7}$ alkanoyl, by $C_{4-7}$ cycloalkylcarbonyl, by $C_{2-7}$ alkoxycarbonyl, by $C_{2-7}$ haloalkoxycarbonyl, by an aryl group or by an aromatic heterocyclic group or $Y^1$ and $Y^2$ together with the nitrogen to which they are attached form an aliphatic heterocyclic group containing from 4 to 8 atoms in the ring and optionally substituted by halogen or alkyl or $Y^1$ and $Y^2$ together form the group $=CHY^3$ wherein $Y^3$ is alkyl, $C_{2-6}$ alkenyl, aryl, an aromatic heterocycle, or amino optionally substituted by alkyl or $Y^1$ is hydrogen and $Y^2$ is alkoxycarbonyl, alkylcarbonyl, optionally substituted aralkyl or a group $-S(O)_nR^6$ where $R^6$ and n are as hereinbefore defined; and $R^7$ and $R^8$, which may be the same or different, are halogen.

2. A compound according to claim 1 wherein $R^1$ is $NH_2$, $N(CH_3)_2$, hydrogen or halogen.

3. A compound according to claim 1 or 2 wherein $R^3$ is $-CN$ or $-CS-NH_2$.

4. A compound according to claim 1 wherein $R^2$ is the group $-S(O)_nR^6$ and $R^6$ is a $C_1-C_4$ haloalkyl group.

5. A compound according to claim 4 wherein $R^6$ is selected from trifluoromethyl, pentafluoroethyl, chlorodifluoromethyl and dichlorofluoromethyl.

6. A compound according to claim 1 wherein $R^7$ and $R^8$ are independently selected from chloro and bromo.

7. An insecticidal or acaricidal composition comprising an insecticidally or acaricidally effective amount of a compound according to claim 1 in association with an insecticidally or acaricidally inert diluent or carrier.

8. A method of combating insect and acarine pests at a locus which comprises treating the locus with an insecticidally or acaricidally effective amount of a composition according to claim 7.

* * * * *